United States Patent [19]

Chopra

[11] Patent Number: 6,153,440
[45] Date of Patent: Nov. 28, 2000

[54] SIMULTANEOUS MEASUREMENT OF FREE TRIIODOTHYRONINE AND FREE THYROXINE BY EQUILIBRIUM DIALYSIS AND IMMUNOASSAY

[75] Inventor: Inder J. Chopra, Calabasas, Calif.

[73] Assignee: The Regents of the University of California, Oakland, Calif.

[21] Appl. No.: 09/158,872

[22] Filed: Sep. 23, 1998

[51] Int. Cl.[7] .......................... G01N 33/53; G01N 33/567; G01N 33/553; G01N 33/552; G01N 33/554

[52] U.S. Cl. .......................... 436/500; 436/504; 436/526; 436/527; 436/518; 436/538; 436/542; 424/1; 424/111; 435/5; 435/7.1; 435/7.22; 435/7.32; 435/7.5; 435/7.23

[58] Field of Search ................................. 436/527, 500, 436/504, 538, 542, 526, 518; 424/1, 111; 435/5, 7.1, 7.22, 7.32, 7.5, 7.23

[56] References Cited

U.S. PATENT DOCUMENTS

| | | | |
|---|---|---|---|
| 3,911,096 | 10/1975 | Chopra | 424/1 |
| 3,928,553 | 12/1975 | Hollander | 424/1 |
| 3,981,981 | 9/1976 | Reunanen | 424/1.5 |
| 4,034,073 | 7/1977 | Weetall | 424/1 |
| 4,108,974 | 8/1978 | Wegfarht et al. | 424/1 |
| 4,225,576 | 9/1980 | Denning et al. | 424/1 |
| 4,229,812 | 10/1980 | Holloway | 367/158 |
| 4,292,296 | 9/1981 | Parsons, Jr. | 424/1 |
| 4,963,256 | 10/1990 | Nelson | 210/232 |
| 4,966,838 | 10/1990 | Ferrua et al. | 435/7 |
| 5,366,859 | 11/1994 | Miyoshi et al. | 435/5 |
| 5,639,670 | 6/1997 | Bergmann et al. | |

OTHER PUBLICATIONS

T. Yamamoto et al. (1975) Folia Endocrinology 20;51(2):76–84.
J.G. Lundgren et al. (1976) Acta Endocrinol. Mar;81(3):487–94.
P. Liu et al. (1978) Sci. Sin (B) Feb;30(2):169–75.
M.L. Brown et al. (1977) J. Nucl. Med. Mar; 18(3):300–4.
Y.S. Wang (1985) Clin. Chem. Apr;31(4):517–22.
C. Blake et al. (1982) Clin. Chem. Jul;28(7):1469–73.
S.P. Haynes et al. (1977) Ann. Clin. Biochem. Jan;14(1)12–5.
T. Mitsuma et al. (1972) Mar 24, 46(6):2107–13.
P. Carayon et al. (1974) Ann Endocrinol May–Jun;35(3)275–6.
J.T. Nicoloffet al. (1972) J. Clin. Invest. Mar;51(3):473–83.
J.C. Nelson et al. (1979) J. Clin. Lab. Invest. 39:53–59.
R. Kannan et al. (1984) Endocrinology 115:1710–1716.
S. Melmed et al. (1981) J. Clin. Enocrinol. Metab. 53:997–1001.
J.C. Jaune et al. (1996) Thyroid 6:76–83.
M.I. Surks et al. (1988) J. Clin. Endocrinol Metab. 67:1031–9.
J. Faber et al. (1997) J. Clin. endocrinol. Metabl, 65:316–320.
I.J. Chopra et al. (1979) Ann Intern Med. 90:905–12.

F. Bermudez et al. (1995) J. Clin. Endocrinol Metab. 41:27–40.
J.R. Stockigt et al. (1913) 29:1408–10.
R. Ekins et al. (1985) Lancet 1:782.
M.N. Alexander (1986) Clin. Chem. 32:417.
I.J. Chopra et al. (1980) J. Clin. Endocrinol Metab. 51:135–143.
T. Olsen (1979) Scand. J. Clin. Lab. Invest 39:53–59.
S.W. Spaulding et al. (1972) J. Clin. Endocrinol Metab. 34:974–82.
C.H.G. Irving (1974) J. Clin. Endocrinol Metab. 38:655–62.
I.J. Chopra (1974) J. Cl in. Invest. 54:583–592.
I.J. Chopra (1996) Thyroid 6(4):255–259.
J.C. Nelson et al. (1988) Clin Chem 34(9):1737–1744.
IT Chopra (1997) Journal of Clinical Endocrinology and Metabolism 82(2):329–334.
Docter. R, et al, Free thyroxine assessed with three assays in sera of patient with nonthyrodial illness and subjects with abnormal concentrations of thryoxine–binding proteins. Clinical chemistry, vol. 39, No.8, pp. 1668–1674, 1993.

*Primary Examiner*—Nita Minnifield
*Assistant Examiner*—Padma Baskar
*Attorney, Agent, or Firm*—Gates & Cooper

[57] ABSTRACT

The present invention provides methods for the simultaneous measurement of triiodothyronine ($T_3$) and thyroxine ($T_4$) in biological fluids such as serum by direct equilibrium dialysis and immunoassay. Specifically, the method comprises dialyzing the serum sample to equilibrium in a physiological buffer system so that the free $T_3$ and the free $T_4$ are separated from $T_3$ and $T_4$ bound to serum proteins. The method further comprises combining a measured quantity of the dialyzed serum sample having free $T_3$ and free $T_4$ with reagents comprising a measured quantity of $T_3$ labelled with a detectable marker and a measured quantity of $T_4$ labelled with a detectable marker; an anti-$T_3$ antibody of sufficient specificity and in sufficient quantity to bind a measurable quantity of the free $T_3$, and an anti-$T_4$ antibody of sufficient specificity and in sufficient quantity to bind a measurable quantity of the free $T_4$. The method then comprises allowing reaction of the free $T_3$ and the free $T_4$ and the labelled $T_3$ and the labelled $T_4$, with the anti-$T_3$ antibody and the anti-$T_4$ antibody to proceed substantially to equilibrium to thereby produce antibody bound labelled $T_3$ and antibody bound labelled $T_4$. Finally, the method comprises separating the unbound labelled $T_3$ from the antibody bound labelled $T_3$ and the unbound labelled $T_4$ from the antibody bound labelled $T_4$; and determining the levels of $T_3$ and $T_4$ in the sample by comparing relative amounts of antibody bound labelled $T_3$ and $T_4$ and unbound labelled $T_3$ and $T_4$. In one embodiment of this method, the assay is a radioimmunoassay.

18 Claims, 4 Drawing Sheets

| GROUP | FREE T3* SEPARATE | FREE T3 SIMULTANEOUS | FREE T4 SEPARATE | FREE T4* SIMULTANEOUS |
|---|---|---|---|---|
| NORMAL SUBJECTS | 256 ±11(53) | 285 ±11(53) | 1.03 ±0.03(36) | 1.08 ±0.04(36) |
| HYPOTHYROID | 261 ±21(26) | 231 ±18(26) | 0.52 ±0.06(21) | 0.4 ±0.03(21) |
| HYPERTHYROID | 1181 ±143(18) | 1123 ±134(13) | 3.61 ±0.35(8) | 4.17 ±0.88(8) |
| NONTHYROID ILLNESS | 268 ±42(18) | 262 ±29(18) | 1.71 ±0.20(12) | 1.58 ±0.27(12) |

\* MEAN ± SEM
\*\* MEASURED SIMULTANEOUSLY WITH FREE T3
\*\*\* MEASURED SIMULTANEOUSLY WITH FREE T4

FIG. 3

| GROUP | N | FREE T4 (ng/dl) | FREE T3 (pg/dl) | FT3/FT4 | % FREE T3 | TOTAL T3 (ng/dl) | % FREE T4 | TOTAL T4 | REVERSE T3 (ng/dl) | TSH (U/ml) |
|---|---|---|---|---|---|---|---|---|---|---|
| NORMAL SUBJECTS | 54 | 1.2±0.04 (0.70-2.3) | 285±10 (134-454) | 0.26±0.01 (0.14-0.45) | 0.30-0.01 (0.16-0.52) | 113±2.7 (84-160) | 0.015±0.003 (0.01-0.03) | 8.1±0.47 (5-11) | 12±0.91 (6-31) | 1.8±0.16 (0.23-5.5) |
| HYPERTHYROID | 20 | 3.6±0.4 d (1.8-9.6) | 1033±98 e (593-2134) | 0.32±0.03 (0.07-0.51) | 0.50±0.04 b (0.27-0.90) | 214±25 e (85-560) | | | | 0.10±0.01 c (0.05-0.20) |
| HYPOTHYROID | 26 | 0.40±0.04 e (0.10-0.70) | 235±24 (27-597) | 0.82±0.14 e (0.13-2.7) | 0.30±0.03 (0.11-0.82) | 90±83 c (19-175) | | | | 37±13 (0.10-293) |
| HYPOTHYROID WITH HIGH TSH | 12 | 0.40±0.06 e (0.10-0.70) | 175±23 e (67-378) | 0.48±0.37 (0.13-2.5) | 0.30±0.05 e (0.17-0.82) | 58±59 e (19-95) | | | | 77±23 d (10-293) |
| HYPOTHYROID WITH LOW AND NORMAL TSH | 14 | 0.40±0.04 e (0.15-0.58) | 279±37 (27-597) | 0.81±0.19 (0.18-2.7) | 0.20±0.02 c (0.11-0.48) | 117±9.6 e (24-169) | | | | 2.1±0.5 (0.1-4.5) |
| NONTHYROID ILLNESS | 25 | 1.6±0.19 (0.66-4.0) | 273±28 (62-575) | 0.19±0.02 d (0.03-0.38) | 0.70±0.06 e (0.26-1.4) | 46±5.0 e (10-84) | 0.23±0.005 e (0.01-0.04) | 8.3=0.54 (1.9-15) | 109±14 e (40-330) | 2.2±0.55 (0.05-11) |
| PATIENTS WITH SEVERE NTI* | 7 | 1.45±0.23 a (0.52-2.0) | 237±81 (62-575) | 0.17±0.05 a (0.03-0.38) | 0.86±0.07 e (0.62-1.20) | 26±8.5 e (10-70) | 0.03±0.01 (0.02-0.06) | 3.5=0.49 e (1.9-5.0) | 146±37 e (63-330) | 1.5±0.8 (0.05-5.3) |
| PATIENTS WITH MODERATE NTI** | 18 | 1.70±0.25 b (0.68-4.0) | 296±28 (100-516) | 0.21±0.02 (0.08-0.38) | 0.59±0.07 b (0.26-1.31) | 55±4.8 e (19-84) | 0.02±0.003 (0.01-0.04) | 9.9±0.6 b (5.9-15) | 111±18 e (40-330) | 2.8±0.7 (0.13-10.9) |
| NEWBORN CORD BLOOD | 18 | 1.40±0.08 e (0.90-2.2) | 204±22 d (62-365) | 0.10±0.02 e (0.06-0.29) | 0.40±0.05 (0.19-0.81) | 50±3.3 (28-74) | | | 183±12 e (112-299) | 6.3±0.59 (3.4-12) |

X = MEAN±SEM; Y = TOTAL T4 AND % FREE T4 DATA ARE IN 30 (OUT OF 54) NORMAL SUBJECTS AND 20 (OUT OF 25) NTI PATIENTS (5 WITH SEVERE NTI AND 15 WITH MODERATE NTI)
Cf NORMAL SUBJECTS 2p = a≤0.1; b≤0.05, c≤0.01; d≤0.005; e≤0.001
* = PATIENTS WHO DIED (n=6) AND/OR HAD LOW SERUM TOTAL T4 (n=3); ** = PATIENTS WHO WERE DISCHARGED FROM HOSPITAL AND/OR HAD NORMAL SERUM TOTAL T4

FIG. 4

SIMULTANEOUS MEASUREMENT OF FREE TRIIODOTHYRONINE AND FREE THYROXINE BY EQUILIBRIUM DIALYSIS AND IMMUNOASSAY

BACKGROUND OF THE INVENTION

1. Field of the Invention

This invention relates to immunoassay methods for the quantitative determination of triiodothyronine ($T_3$) and thyroxine ($T_4$) in biological fluids. In particular, the present invention provides methods for the simultaneous measurement of these hormones by direct equilibrium dialysis and immunoassay.

2. Description of Related Art

The thyroid gland is an endocrine gland situated at the base of the neck which synthesizes two peptidic thyroid hormones, triiodothyronine ($T_3$) and thyroxine ($T_4$), by the condensation of two molecules of iodized thyrosine, monoiodothyrosine and diiodothyrosine. Thyroid hormone are synthesized and stored in the thyroid bound to the thyroid protein, thyroglobulin, until they are released into the circulation by a proteolytic process. The majority of thyroid hormone is then carried in the serum bound to three proteins: TBG (thyroxine-bonding globulin), TBPA (thyroxine-bonding prealbumin) and albumin. However, a small proportion (about 0.03% each of $T_3$ and $T_4$) of total thyroid hormone exists in the circulation in a free (unbound) form.

The circulating thyroid hormones exert their activity on several target tissues in the body. Thyroid hormones physiologically affect the tissues by stimulating cellular oxygen consumption, lipid and glucose metabolism, and influencing normal growth during development. However, it is generally assumed that it is only the free form, and not the bound form, of the thyroid hormones that can enter the cells to exert their physiological action.

A determination of free circulating thyroid hormone levels is critical to an appropriate assessment of thyroid function. The methods available for the quantitative determination of circulating concentrations of thyroid hormones are important for diagnosing hyperthyroidism or hypothyroidism. However, the determination of the total $T_4$ or $T_3$ levels as an indication of thyroid function may lead to erroneous diagnosis of thyroid disorder. For example, conditions which result in elevated levels of thyroid hormone binding proteins (such pregnancy, liver diseases and elevated estrogen or opiate levels) will proportionally result in elevated levels of bound thyroid hormones in the serum being detected in the assay. Elevated bound thyroid hormone levels may, thus, lead to a misdiagnosis of a patient as hyperthyroid, even where levels of free $T_3$ or $T_4$ in the serum may be normal. Therefore, it is important to be able to determine the level of free $T_3$ and $T_4$ which is biologically active in the patient to more accurately assess the status of the thyroid gland.

While considerable effort has been directed at the development of various assays for $T_3$ and $T_4$, there are a number of problems associated with existing assays for measuring these thyroid hormones. What is needed in the art is a simple assay which overcomes problems associated with existing assays and allows the simultaneous determination of free $T_3$ and free $T_4$ in a single serum sample. The invention described herein overcomes the problems associated with art accepted assays by providing simple and effective methods for the simultaneous immunological quantitative determination of the $T_3$ and $T_4$ thyroid hormones.

SUMMARY OF THE INVENTION

The present invention provides a practical method for measuring free $T_3$ and $T_4$ levels simultaneously in undiluted serum by direct equilibrium dialysis/immunoassay. The method enhances the cost effectiveness of free $T_3$ and $T_4$ measurements, when performed together, by reducing the need for sample volume, dialysis cells, reagents and technician time. In addition, as disclosed herein, the described methods are highly effective for the measurement of free thyroid hormones in various clinical conditions of health and disease.

In one embodiment, the invention consists of a immunoassay method for the simultaneous measurement of free $T_4$ and $T_3$ in a serum sample. The method comprises the steps of dialyzing the serum sample to equilibrium in a physiological buffer system so that the free $T_3$ and the free $T_4$ are separated from $T_3$ and $T_4$ bound to serum proteins. The method further comprises combining a measured quantity of the dialyzed serum sample having free $T_3$ and free $T_4$ with reagents including a measured quantity of $T_3$ labelled with a detectable marker and a measured quantity of $T_4$ labelled with a detectable marker; an anti-$T_3$ antibody of sufficient specificity and in sufficient quantity to bind a measurable quantity of the free $T_3$, and an anti-$T_4$ antibody of sufficient specificity and in sufficient quantity to bind a measurable quantity of the free $T_4$. The method then comprises allowing reaction of the free $T_3$ and the free $T_4$ and the labelled $T_3$ and the labelled $T_4$, with the anti-$T_3$ antibody and the anti-$T_4$ antibody to proceed substantially to equilibrium to thereby produce antibody bound labelled $T_3$ and antibody bound labelled $T_4$. Finally, the method comprises separating the unbound labelled $T_3$ from the antibody bound labelled $T_3$ and the unbound labelled $T_4$ from the antibody bound labelled $T_4$; and determining the levels of $T_3$ and $T_4$ in the sample by comparing relative amounts of antibody bound labelled $T_3$ and $T_4$ and unbound labelled $T_3$ and $T_4$. In one embodiment, the immunoassay is a radioimmunoassay.

In a variation on the embodiment described above, a measured quantity of exogenous unlabelled $T_3$ is added to the serum sample in order to place the overall concentration of $T_3$ in a range that allows for an optimal determination of its concentration. In another embodiment of the invention, the matrix to which the anti-$T_3$ or anti-$T_4$ antibody is bound comprises a portion of a container in which a radioimmunoassay is performed. In a specific embodiment of the invention, the physiological buffer system comprises about 130 mmol of sodium, about 4.3 mmol of potassium, about 1.9 mmol of calcium, about 1.0 mmol of magnesium, about 98 mmol of chloride, about 1.3 mmol of phosphate, about 1.3 mmol of sulfate, about 5.4 mmol of lactate, about 3.3 mmol of glutamate, and about 8 mmol of urea. In a variation on this embodiment, the buffer system further comprises preservatives and gelatin.

In more specific embodiment of the invention, the incubation step is carried out at a temperature of about 4° C. for a period of about 20 hours. In yet another specific embodiment, the label is iodine-125. Additional embodiments of the invention include those where the antibody bound radioactive thyroid hormone to be measured is separated from said free radioactive thyroid hormone by precipitation of the $T_3$ or the $T_4$ with an agent selected from the group consisting of: a second antibody, gamma globulin, a charcoal suspension and polyethylene glycol.

BRIEF DESCRIPTION OF THE DRAWINGS

FIG. 4 is a Table which provides data on the serum concentrations of free $T_4$, free $T_3$, % free $T_4$, total $T_4$, reverse $T_3$ and/or TSH in various groups of patients studied.

DETAILED DESCRIPTION OF THE INVENTION

Definitions

As used herein the term "free" applied to $T_3$ and $T_4$ means that the reference is to $T_3$ and $T_4$ not bound to carrier proteins such as thyroxine-bonding globulin, thyroxine-bonding prealbumin and albumin.

As used herein the term "physiological buffer system" means dialysate buffers that are designed to approximate the composition of a protein-free ultrafiltrate of normal human serum, at least for those compounds present in serum at a concentration of 1 mmol/L or more, except that nonessential molecules such as glucose may be omitted and preservative may be included.

As used herein the term "matrix" is used in its broadest sense and includes any materials to which an antibody may be attached including the walls of a container such as a polystyrene tube as well as any of the beads or particles known in the art.

Availability of practical, convenient and cost effective methods for direct measurement of free $T_3$ and free $T_4$ serum concentration is important to the appropriate diagnosis and treatment of thyroid disease. The invention disclosed herein is based on the unexpected discovery that the simultaneous detection of $T_3$ and $T_4$ can be achieved in this method without problematic interactions between multiple antibodies and multiple analytes. The present invention renders the detection of biologically active thyroid hormone more efficient when both measurements are required to assess thyroid function. Specifically, this method provides a practical, sensitive and selective method for simultaneous measurement of free $T_3$ and $T_4$ in undiluted serum by direct equilibrium dialysis/RIA.

The method for simultaneous measurements of free $T_3$ and $T_4$ utilizes fewer reagents and dialysis cells, and reduces the necessary sample volume and time for sample handling, than would be required where independent measures of the thyroid hormones are conducted. Further, the method provides an assay whose sensitivity is not compromised by combining the assay processes. Specifically, serum free $T_4$ concentration in samples when measured separately do not differ appreciably from that measured together with free $T_3$; and serum free $T_3$ concentration in samples measured separately does not differ appreciably from that measured together with free $T_4$. These attributes make the combined simultaneous assay a more practical, cost-effective and sensitive assay compared to two separate measurements of free $T_3$ and $T_4$.

In various embodiments of the present invention, the method comprises immunoassays, and in particular, radio-immunoassays for measuring $T_3$ and $T_4$. The general field of immunoassays is well developed and those skilled in the art have access to a wide variety of various embodiments, see e.g. *Current Protocols In Molecular Biology*, Volume 2, Units 9, 11 and 18, Frederick M. Ausubul et al. eds. In addition, there are a number of protocols for specifically quantitating thyroid hormones including those disclosed in U.S. Pat. Nos. 3,911,096; 3,928,553; 4,034,073; 4,108,974; 4,225,576; 4,229,812; 4,292,296; 4,966,838 and 5,366,859, all of which are incorporated herein by reference.

In various embodiments of the present invention, the method comprises dialyzing a serum sample containing thyroid hormone. Various methods and materials used in dialysis are well known in the art, see e.g. *Current Protocols In Molecular Biology*, Volume 2, Units 10 and 12, Frederick M. Ausubul et al. eds. In addition, there are a number of protocols involving dialysis in the context of radioimmunoassays including those disclosed in U.S. Pat. Nos. 3,981,981 and 4,963,256, which are incorporated herein by reference. In one embodiment of the invention, the sample is dialyzed in acrylic plastic dialysis cells. While an illustrative example of the dialysis cell which can be used is the one used herein and designed by Nelson and Tomei, Quest-Nichols Institute, San Juan Capistrano, Calif., various other dialysis systems that are applicable to the present invention are well known in the art.

The conditions for dialysis approximate the composition of a protein-free ultrafiltrate of normal human serum, at least for those compounds present in serum at a concentration of 1 mmol/L or more, except that certain molecules such as glucose may be omitted and preservatives may be added. An illustrative physiological buffer system includes a dialysis buffer comprising about 130 mmol of sodium, about 4.3 mmol of potassium, about 1.9 mmol of calcium, about 1.0 mmol of magnesium, about 98 mmol of chloride, about 1.3 mmol of phosphate, about 1.3 mmol of sulfate, about 5.4 mmol of lactate, about 3.3 mmol of glutamate, and about 8 mmol of urea. Nelson and Tomei, Clin. Chem. 34/9, 1737–1744 (1988) describe an illustrative specific buffer formulation of dialysate buffer where one liter comprises sodium chloride, about 5.265 grams; 60% syrup of DL-lactic acid, as the sodium salt, 1.0 mL; L-glutamic acid as the monosodium salt, 561 mg; potassium chloride, 224 mg; monopotassium phosphate, 180 mg; calcium chloride●2 $H_2O$, 275 mg; magnesium sulfate●7 $H_2O$, 246 mg; urea, 300 mg; HEPES sodium salt, 5.891 g; HEPES acid 7.190 g; penicillin, 100,000 USP units; streptomycin, 100 mg; sodium azide, 520 mg; gelatin, 500 mg; and rabbit IgG, 200 mg. The pH of such buffers may be adjusted at room temperature with sodium hydroxide or hydrochloric acid to about 7.4. The conditions for dialysis can be selected so that sample is made free from impurities that would otherwise result in artifactually elevated readings of thyroid hormones in the sample. One skilled in the art will appreciate that a variety of variations on such physiological buffer systems are possible and that in approximating physiological conditions, the concentrations of elements such as phosphate and chloride ions important for maintaining these conditions. As such, conditions for dialysis should be selected so that the physiological range of the dialysate is maintained.

After the sample has been dialyzed, the sample can be assayed simultaneously for the thyroid hormones. In one embodiment of the invention, the assay is carried out in polystyrene tubes containing selective antibodies for $T_3$ and $T_4$. In a variation of this embodiment, the tube walls are coated with one antibody (anti-$T_4$) while the other (anti-$T_3$) is in solution. In an alternative embodiment, both antibodies are in solid phase, one is fixed to the walls of the tube (e.g. anti-$T_4$) and the other (e.g. anti-$T_3$) is fixed coated on a bead contained within the tube. Various methods and materials for using antibodies attached to a matrix are well known in the art, see e.g. *Current Protocols In Molecular Biology*, Volume 2, Units 10 and 11, Frederick M. Ausubul et al. eds. A system having both antibodies bound permits simultaneous washing of solid phases for separation of antibody-bound from free hormones and can help make the assays even more time efficient. The antibodies used in this assay can be, but are not limited to, antisera and monoclonal antibodies generated and purified by art accepted methods as described below.

The $T_3$ and $T_4$ antibodies having the desired sensitivity and specificity can comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent can include the $T_3$ and $T_4$ polypeptide or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants, which may be employed, include Freund's complete adjuvant and MPL-TDM adjuvant (monophosphoryl Lipid A, synthetic trehalose dicorynomycolate). Further, polyclonal antibodies can be generated commercially, for example by Genemed Synthesis, Inc. using art accepted methods.

The $T_3$ and $T_4$ antibodies having the desired sensitivity and specificity can, alternatively, be monoclonal antibodies. Monoclonal antibodies can be prepared using hybridoma methods, such as those described by Kohler and Milstein, *Nature* 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include the $T_3$ and $T_4$ polypeptide or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies: Principles and Practice*, Academic Press, (1986) pp. 59–103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Rockville, Md. Human myeloma and mouse-human heteromyeloma cell lines also have been described for the production of human monoclonal antibodies [Kozbor, J. Immunol., 133:3001 (1984); Brodeur et al., *Monoclonal Antibody Production Techniques and Applications*, Marcel Dekker, Inc., New York, (1987) pp. 51–63].

The culture medium in which the hybridoma cells are cultured can then be assayed for the presence of monoclonal antibodies directed against $T_3$ and $T_4$. Preferably, the binding specificity of monoclonal antibodies produced by the hybridoma cells is determined by immunoprecipitation or by an in vitro binding assay, such as radioimmunoassay or enzyme-linked immunoabsorbent assay (ELISA). Such techniques and assays are known in the art. The binding affinity of the monoclonal antibody can, for example, be determined by the Scatchard analysis of Munson and Pollard, Anal. Biochem., 107:220 (1980). Other sources of antibodies may be used such as those found in commercially available kits. An anti-$T_4$ antibody kit may be purchased from the Quest-Nichols Institute (catalogue number 40-2210). An anti-$T_3$ antibody kit may purchased from the Diagnostic Products Corporation (catalogue number TKT31).

General methods and materials used in the purification of antibodies having the desired sensitivity and specificity are well known in the art, see e.g. *Current Protocols In Molecular Biology*, Volume 2, Unit 11, Frederick M. Ausubul et al. eds. In addition, there are a number of specific protocols involving the purification of such highly specific and sensitive antibodies including those disclosed in U.S. Pat. Nos. 3,697,645, 4,264,449 and 5,110,913, which are incorporated herein by reference. The antibodies used in the methods disclosed herein should be purified or otherwise generated or selected such that the cross-reactivity of the assay is minimized. For example, using the antibodies described in the Examples below, free $T_3$, $rT_3$, and $T_2$s crossreacted <0.005% in $T_4$ RIA. $T_4$, M and $T_2$s cross-reacted <0.1% in the $T_3$ RIA.

The samples assayed with the method of this invention can contain a wide range of thyroid hormone concentrations. The samples can comprise standards of $T_3$ and $T_4$ for which the concentration of thyroid hormone in the sample is known. The samples can also comprise an unknown $T_3$ and $T_4$ concentration. In an extended practice of this invention, a known quantity of $T_3$ can be added to the sample of unknown thyroid hormone concentration. The amount of $T_3$ used to spike the sample can be selected so that a final reading of the $T_3$ concentration will result in the steep and most accurate portion of the standard curve for the $T_3$ RIA, and so that the amount of $T_3$ does not appreciably increase the percentage of free $T_3$ in the sample. The samples further comprise labeled $T_3$ and or $T_4$ to quantify the competitive binding of the free thyroid hormone contained in the sample to the antibodies used in the assay. Various methods and materials for labeling proteins are well known in the art, see e.g. *Current Protocols In Molecular Biology*, Volume 2, Units 10 and 11, Frederick M. Ausubul et al. eds. In one embodiment, the label is a radionucleotide. It is well known in the art that proteins in an assay may be labelled with different radionuclides, $I^{125}$, $I^{131}$ and $S^{35}$ for example, in order to distinguish the various proteins within a mixture.

After an incubation period has elapsed for the immunoassay, the method further comprises the quantification of the amount of $T_3$ and $T_4$ present in the sample. In radioimmunoassays, the quantification is performed upon separation of the reacted radioactive-$T_3$-anti-$T_3$ and radioactive $T_4$-anti-$T_4$. A variety of methods for quantifying analytes in a radioimmunoassay are well known in the art, see e.g. U.S. Pat. No. 4,225,576. In one embodiment of the invention, the separation entails separating the fluid (containing the anti-$T_3$) from the tube (containing the anti-$T_4$), and further separation of the reacted radioactive $T_3$ from the unreacted radioactive-$T_3$ by gammaglobulin precipitation.

The invention described herein has a variety of embodiments. One embodiment consists of an immunoassay method for the simultaneous measurement of free $T_4$ and $T_3$ in a serum sample. The method comprises dialyzing the serum sample to equilibrium in a physiological buffer system so that the free $T_3$ and the free $T_4$ are separated from $T_3$ and $T_4$ bound to serum proteins. The method further comprises combining a measured quantity of the dialyzed serum sample having free $T_3$ and free $T_4$ with reagents comprising a measured quantity of $T_3$ labelled with a detectable marker and a measured quantity of $T_4$ labelled with a detectable marker; an anti-$T_3$ antibody of sufficient specificity and in sufficient quantity to bind a measurable quantity of the free $T_3$, and an anti-$T_4$ antibody of sufficient specificity and in sufficient quantity to bind a measurable quantity of the free $T_4$. The method then comprises allowing reaction of the free $T_3$ and the free $T_4$ and the labelled $T_3$ and the labelled $T_4$, with the anti-$T_3$ antibody and the anti-$T_4$ antibody to proceed substantially to equilibrium to thereby produce antibody bound labelled $T_3$ and antibody bound labelled $T_4$. Finally, the method comprises separating the unbound labelled $T_3$ from the antibody bound labelled $T_3$ and the unbound labelled $T_4$ from the antibody bound labelled $T_4$; and determining the levels of $T_3$ and $T_4$ in the sample by comparing relative amounts of antibody bound labelled $T_3$ and $T_4$ and unbound labelled $T_3$ and $T_4$. In one embodiment of this method, the assay is a radioimmunoassay.

In a variation on the embodiment described above, a measured quantity of exogenous unlabelled $T_3$ is added to the serum sample in order to place the overall concentration of $T_3$ in a range that allows for an optimal determination of its concentration. In another embodiment of the invention, the matrix to which the anti-$T_3$ or anti-$T_4$ antibody is bound comprises a portion of a container in which the radioimmunoassay is performed. In a specific embodiment of the invention, the physiological buffer system comprises about 130 mmol of sodium, about 4.3 mmol of potassium, about 1.9 mmol of calcium, about 1.0 mmol of magnesium, about 98 mmol of chloride, about 1.3 mmol of phosphate, about 1.3 mmol of sulfate, about 5.4 mmol of lactate, about 3,3 mmol of glutamate, and about 8 mmol of urea.

In another specific embodiment of the invention, the incubation step is carried out at a temperature of about 4° C. for a period of about 20 hours. In yet another specific embodiment, the label is iodine-125. Additional embodiments of the invention include those where the antibody bound radioactive thyroid hormone to be measured is separated from said free radioactive thyroid hormone by precipitation of the $T_3$ or the $T_4$ with an agent selected from the group consisting of: a second antibody, gamma globulin, a charcoal suspension and polyethylene glycol.

Yet another specific embodiment of the invention consists of an radioimmunoassay method for the simultaneous measurement of free thyroxine $T_4$ and $T_3$ in a serum sample. The method comprises dialyzing the serum sample to equilibrium in a physiological buffer system so that the free $T_3$ and the free $T_4$ are separated from $T_3$ and $T_4$ bound to serum proteins. The method further comprises combining a measured quantity of the dialyzed serum sample having free $T_3$ and free $T_4$ with reagents comprising a measured quantity of radiolabeled $T_3$ and a measured quantity of radiolabeled $T_4$ as well as an anti-$T_3$ antibody of sufficient specificity and in sufficient quantity to bind a measurable quantity of the $T_3$, and an anti-$T_4$ antibody of sufficient specificity and in sufficient quantity to bind a measurable quantity of the $T_4$, wherein at least one antibody specific for $T_3$ or $T_4$ is bound to a matrix, and then allowing reaction of the free $T_3$ and the free $T_4$ and the radioactive $T_3$ and the radioactive $T_4$, with the anti-$T_3$ antibody and the anti-$T_4$ antibody to proceed substantially to equilibrium to thereby produce antibody bound radioactive $T_3$ and antibody bound radioactive $T_4$. The method then comprises separating the antibody bound radioactive $T_3$ from the antibody bound radioactive $T_4$, separating the unbound radioactive $T_3$ from the antibody bound radioactive $T_3$ and the unbound radioactive $T_4$ from the antibody bound radioactive $T_4$; measuring the quantity of antibody bound radioactive $T_3$ and $T_4$. Finally, the method comprises preparing a $T_3$ standard curve with known amounts of $T_3$ and preparing a $T_4$ standard curve with known amounts of $T_4$; and finally comparing the quantity of radioactive $T_3$ measured with a known amount of $T_3$ read from the $T_3$ standard curve and correlating the quantity of radioactive $T_4$ measured with a known amount of $T_4$ read from the $T_4$ standard curve.

Embodiments of the methods disclosed herein were compared with established methods to assess the levels of $T_3$ and/or $T_4$ in a number of clinical states. These comparative assays were undertaken to address the ability of the various reagents to interact in the presence of potentially incompatible reagents. Specifically, absent such comparative studies, there is no way to determine whether, for example, under a specific set of conditions, anti-$T_3$ antibody will inhibit the association of the sample $T_4$ and the labelled $T_4$ with the anti-$T_4$ antibody. These studies also confirm that, in the same reaction vessel, the anti-$T_4$ antibody does not inhibit the association between the labelled $T_3$, the $T_3$ from the sample and the anti-$T_3$ antibody. The studies presented in the Examples below detail the unexpected findings that the combined simultaneous assay disclosed herein produces results that are equivalent to known assays involving the determination of a single analyte.

Using the disclosed embodiments, the measurements of free $T_4$ concentration permit the accurate diagnosis of both hyperthyroidism and hypothyroidism in most instances. Moreover, the disclosed methods have been used to confirm previous studies which showed that free $T_4$ concentration by similar techniques is normal in patients with nonthyroid illness (7,11,12). J. C. Nelson, et al., J Clin Lab Invest. 1979;39:53–59; J. C. Nelson, et al., Clin Chem 1988;34:1737–44; Coming Nichols Institute, San Juan Capistrano, Calif., J Clin Endocrinol Metab. 1988;67:1031–9. In addition, using the described radioimmunoassay, elevated free $T_4$ was observed in patients taking amiodarone and heparin which is consistent with studies showing that amiodarone treatment is known to decrease the metabolic clearance of $T_4$ and to elevate serum levels of total and free $T_4$ concentrations. R. Kannan, et al., Endocrinology. 1984; 115:1710–1716; S. Melmed, et al., J. Clin. Endocrinol. Metab. 1981;53:997–1001. Data using the described inventions are also consistent with studies showing that heparin increases free $T_4$ concentration by an in vitro phenomenon resulting from liberation of fatty acids from triglycerides and fatty acids causing in vitro displacement of $T_4$ from thyronine binding globulin (TBG). J. C. Jaume, et al., Thyroid 1996;6:76–83.

The methods disclosed herein were also used to verify previous studies indicating that free $T_3$ concentration is essentially uniformly elevated in hyperthyroidism, while it is often in the normal range in hypothyroidism. Using the disclosed invention, essentially normal levels of free $T_3$ concentration were found in most (21/25, ~84%, FIG. 2) patients with NTIs and in 15 of 18 (~83%, FIG. 2) newborn cord blood sera. This was the case even when total $T_3$ was clearly decreased, in all 43 of these sera. It is possible that NEFA generated in vitro during prolonged (~18 hours) equilibrium dialysis of sera (24, 25) artefactually increased free $T_3$ in patients from values which may have been otherwise low or low normal. However, is unlikely, because i) a similar situation in normal sera would have adjusted the normal range for free $T_3$; ii) free $T_4$ values would have been affected similarly but this was not the case as free $T_4$ was in the normal range or low; iii) tracer dialysis techniques which also employ prolonged equilibrium dialysis have previously recorded low values for serum free $T_3$ concentration in NTI; and iv) other recent studies using ultrafiltration techniques, which do not employ prolonged incubation needed for equilibrium dialysis, have also demonstrated normal free $T_3$ (and free $T_4$) concentration in patients with low $T_3$ syndrome of NTIs, M. I. Surks, et al., J Clin Endocrinol Metab. 1988;67:1031–9; J. Faber, et al., J. Clin. Endocrinol. Metab. 1987;65:315–320.

Where practitioners have employed known methods utilizing tracer dialysis methods, the labeled analog methods or the $T_3$ resin uptake ratio system for calculating free $T_3$ index have suggested low free $T_3$ concentration values in NTI sera. Problems with the analog methods have been mentioned above and they have been reviewed extensively. I. J. Chopra, et al., Ann Intern Med., 1979;90:905–12; F. Bermudez, et al., J Clin Endocrinol Metab. 1995;41:27–40; J. R. Stockigt, et al., 1913;29:1408–10; R. Ekins, et al., Lancet 1985;I:782; M. N. Alexander, Clin Chem 1986;32:417. The data of this study are consistent with several previous studies showing substantial differences between free hormone measurements estimated by index system and those measured by equilibrium dialysis and between measurements of free $T_4$ concentration derived from systems using tracer dialysis and those using equilibrium dialysis/(RIA). I. J. Chopra, et al., Ann Intern Med., 1979;90:905–12; I. J. Chopra, et al., J Clin Endocrinol Metab. 1980;51;135–143; J. C. Nelson, et al., J Clin Lab Invest. 1979;39:53–59; J. C. Nelson, et al., Clin Chem 1988;34:1737–44; Coming Nichols Institute, San Juan Capistrano, Calif., J Clin Endocrinol Metab. 1988;67:1031–9. The basis for the difference is not known. It may be related in part to the impurities in the tracer(s) influencing the dialysable fraction of $T_4$ (or $T_3$), effect of buffer systems employed previously, effect of dilution of sera for tracer dialysis and/or combination of these factors. There was little or no dilution of samples in the present method and the buffer system employed in our study has been shown to maintain serum analytes in a physiological range. J. C. Nelson, et al., Clin Chem 1988;34:1737–44; I. J. Chopra, et al., Thyroid 1996;6:255–259. Normal serum free $T_3$ in NTI patients was observed when the NTI was moderately severe or when it was severe enough to be fatal. A previous study of a small number (n=9) of NTI patients by a free $T_3$ assay showed both subnormal (n=6) and normal values (n=3). I. J. Chopra, et al., Thyroid 1996;6:255–259. When all available data is combined, it seems that serum free $T_3$ concentration is in the normal range in ~71% (24/34) of NTI patients and low in ~29% (10 of 34) patients. Similarly, combining all available data in newborn cord blood serum suggests that serum free $T_3$ concentration is clearly in the normal range in ~69% (20 of 29) and low in the remaining ~31% newborn cord blood sera.

Findings of normal free $T_3$ (and free $T_4$) in a majority of NTI sera suggest an explanation for the common finding of clinical euthyroidism in NTI patients and in the newborn despite clearly low serum total $T_3$ (and low total $T_4$ in some cases ) (See FIG. 4). Studies showing that % free $T_3$ is elevated in patients with NTIs and in newborns (FIG. 4) suggest that a decrease in serum binding contributes importantly to low total $T_3$ in patients with NTIs and in newborns.

Recent studies have suggested that at least some patients with the nonthyroid illness syndrome are hypothyroid and may benefit from treatment with thyroid hormone. The present study suggests that the use of the methods disclosed herein in the direct measurement of free $T_3$ and free $T_4$ concentration with equilibrium dialysis (RIA) may help identify candidates for such treatment with thyroid hormone.

As illustrated above, the present invention provides a practical method for measuring free $T_3$ and $T_4$ levels simultaneously in undiluted serum by direct equilibrium dialysis/ RIA. Specifically, by omitting a number of steps taught in assays known in the art while retaining its functionality, the method enhances the cost effectiveness of free $T_3$ and $T_4$ measurements, when performed together, by reducing the need for sample volume, dialysis cells, reagents and technician time. In addition, by eliminating the need for problematical reagents such as radioactive tracers, the disclosed assays overcome a number of difficulties associated with the use of these reagents in previously disclosed assays.

EXAMPLES

The present invention provides an assay for the measurement of free $T_3$ and $T_4$ concentration. One example of the clinical conditions for which this assay is useful is the detection and diagnosis of hyperthyroidism and hypothyroidism. The present invention is further detailed in the following Examples, which are offered by way of illustration and are not intended to limit the invention in any manner. All patent and literature references cited in the present specification are hereby incorporated by reference in their entirety.

Example 1

Materials for the Simultaneous Determination of $T_3$ and $T_4$ by Equilibrium Dialysis and Radioimmunoassay Dialysis Cells Acrylic plastic dialysis as designed by Nelson and Tomei were purchased from Quest-Nichols Institute, San Juan Capistrano, Calif. (catalogue number 30-0652). See also Nelson, et al., J Clin Lab Invest. 1979;39:53–59; T. Olsen, Scand J Clin Lab Invest. 1979;39:53–59; S. W. Spaulding, et al., J Clin Endocrinol Metab. 1972;34:974–82; C. H. G. Irving, J Clin Endocrinol Metab. 1974;38:655–62; J. C. Nelson, et al., Clin Chem 1988;34:1737–44.

Dialysis Buffer

A buffer available commercially for measurement of free $T_4$ by equilibrium dialysis (Quest-Nichols Institute, San Juan Capistrano, Calif.) was employed. ("$T_4$ dialysis buffer reagent L", catalogue number 30-0650). This buffer system has been shown to maintain serum analytes in a physiological range. J. C. Nelson, et al., J Clin Lab Invest. 1979;39:53–59; J. C. Nelson, et al., Clin Chem 1988;34:1737–44; Coming Nichols Institute, San Juan Capistrano, Calif., J Clin Endocrinol Metab. 1988;67:1031–9.

Equilibrium Dialysis

Buffer (2.4 ml) was placed into the dialysis compartment of the dialysis cell. Dialysis was initiated by introducing 200 μl test serum into the retentate compartment. The cell was incubated at 37° C. in an incubator for ~18 h. Previous studies had shown that equilibrium was reached in ~14 hours of dialysis. After completion of dialysis, the retentate compartment of the cell was removed and free $T_3$ and free $T_4$ concentration were measured in 0.8 to 1.0 mL of the dialysate by sensitive RIAs.

Preparation of Test Sera

Serum specimens were used in equilibrium dialysis with addition of $T_3$ in a final concentration of 200 ng/dl. Typically, 30 µl of a solution containing 20 ng $T_3$/mL buffer were added to 300 µL serum and the mixture was incubated for 15 min. at room temperature. Two hundred microliters of the $T_3$-spiked serum was used for dialysis. Spiking of serum with $T_3$ was done to obtain a reading of free $T_3$ in the steep and more accurate portion of the standard curve of our $T_3$ RIA. Addition of this amount of $T_3$ does not appreciably increase % free $T_3$ in serum.

Standards $T_3$ and other thyroid hormone analogs were purchased from Sigma Chemical CO., St. Louis, Mo. $T_3$ was dissolved in 0.01 M sodium hydroxide and concentrations for use in the assay were prepared in the assay buffer. Since free $T_3$ assay calibrations have not yet been standardized and corrections are needed for hygroscopic water gain, we adjusted our $T_3$ standard to make it comparable to that available commercially in total $T_3$ RIA kit (Diagnostic Products Corporation, Los Angles, Calif.) (catalogue number TKT31). $T_4$ standards were purchased in kits for $T_4$ measurement from the Quest-Nichols Institute (San Juan Capistrano, Calif., catalogue number 40-2210).

Example 2

Methods for the Determination of $T_3$ and $T_4$ by Equilibrium Dialysis and Radioimmunoassay Sensitive RIAs of $T_3$ and $T_4$ Kits for measurement of free $T_4$ were purchased from Quest-Nichols Institute (San Juan Capistrano, Calif.) and simultaneous RIAs of free T3 and free $T_4$ were set up in tubes coated with anti-$T_4$ antibody. Our sensitive RIA of T3 has been described previously. I. J. Chopra, et al., Thyroid 1996;6:255–259. Anti-$T_4$ antibody coated tubes were labeled for each sample, standard or control and various reagents were added in the following order: i) 800 µl of $T_4$ standards (containing 2 pg to 80 pg $T_4$) and 100 µl of $T_3$ standards (containing one pg to 100 pg $T_3$) to tubes for standard curves; ii) 800 µl of the dialysate to tubes for unknown specimens; iii) 100 µl of assay buffer to tubes for unknown specimens to render volume equal to that in tubes for standards; iv) 50 µl of anti-$T_3$ antibody (final dilution ~1/300,000); anti-$T_4$ antibody was already coated on the walls of tubes; v) 50 ul of 125I-$T_4$ solution (SA 5700 µCi/µg or ~400 Ci/mmol, ~50,000 CPM); vi) 50 µl of 125I-$T_3$ solution (SA 3300 µCi/µg or 2200 Ci/mmol, ~25–30,000 CPM). The final assay volume was 1.05 ml. Each assay included two anti-$T_4$ antibody coated tubes, which contained anti-$T_3$, radioactive $T_4$, radioactive $T_3$ and assay buffer without standard $T_4$ or $T_3$ (100% tubes) and two plain non-antibody-coated tubes, polystyrene tubes which contained no anti-$T_4$ (or anti-$T_3$) or standard $T_4$ (or $T_3$) (0% tubes). All tubes were vortexed and incubated overnight at 4° C. for ~20 hours. About 950 µl of the incubation volume was transferred to separate 10×75 mm glass tubes for precipitation of anti-$T_3$ bound radioactive $T_3$. The original polystyrene assay tubes were then washed twice by dispensing 2.0 ml of working wash solution from the kit into each tube and completely aspirating the liquid from each tube.

Each tube was then counted for one minute. The standard curve for free $T_4$ was prepared as suggested by the kit manufacturer and free $T_4$ was concentration in the specimen was read from the curve. $T_3$, 3,3',5'-$T_3$ (reverse $T_3$, r$T_3$) and diiodothyronines ($T_2$s) crossreacted <0.005% in $T_4$ RIA. Our sensitive $T_3$ RIA for free $T_3$ has been described previously (Chopra et al., Thyroid 6:255, 1996). $T_4$, M and $T_2$s crossreacted <0.1% in our $T_3$ RIA.

To 10×75 mm glass tubes containing 950 µl of incubation volume, we added previously tittered goat anti-rabbit gammaglobulin (second antibody ~100 µl) and 10% polyethylene glycol (~600 µl) to separate bound radioactive $T_3$ from free radioactive $T_3$ (or $T_4$), as previously described. I. J. Chopra, et al., J. Clin. Endocrinal. Metab. 1991;75:189–194. It should be noted that anti-$T_4$ antibody was located only on the walls of assay tubes and no antibody bound $T_4$ was expected to be present in the incubation medium subjected to treatment with the second antibody. Bound $^{125}$I-$T_3$ in the precipitate was counted and a standard curve was prepared for free $T_3$ and its concentration in the dialysate was read from the standard curve. I. J. Chopra, et al., Thyroid 1996;6:255–259; I. J. Chopra, et al., J. Clin. Endocrinal. Metab. 1991;75:189–194. Since specimens had been spiked with ~200 ng/dl of nonradioactive $T_3$, free $T_3$ measured in a specimen was divided by total $T_3$ in serum, i.e. $T_3$ originally present in serum, plus added 200 ng/dl $T_3$ to obtain percent free $T_3$. Total $T_3$ in serum was determined by a specific RIA. It was multiplied by percent free $T_3$ to calculate free $T_3$ concentration in the original serum. Previous and current detailed studies had demonstrated that addition of $T_3$ in a concentration of 200 ng/dl did not increase the percent free $T_3$ in the pooled serum of normal subjects or hospitalized patients. $T_4$, r$T_3$, and T2s crossreacted <0.1% in our $T_3$ RIA.

Augmentary Assays

Serum total $T_3$ concentration was measured by RIA using a commercial kit (Diagnostic Products Corporation, Los Angeles, Calif.). Serum TSH concentration was measured by immunoradiometric assay using a kit from the Quest-Nichols Institute (San Juan Capistrano, Calif., catalogue number 401-2160). Serum r$T_3$ concentration was measured by a modification of the assay described previously. I. J. Chopra, J Clin Invest. 1974;54:583–592. Serum total $T_4$ was measured at UCLA Clinical Laboratories. Percent free $T_4$ was determined by dividing serum free $T_4$ concentration by serum total $T_4$ concentration.

Sources of Sera

Sera were collected from 54 healthy normal adult volunteers and/or blood donors, 20 hyperthyroid patients with Graves' disease, 26 hypothyroid patients, and 25 patients with the low $T_3$ syndrome. The last group of patients were hospitalized for systemic illnesses including liver disease (3), renal failure (2), heart disease (heart failure, cardiomyopathy, arrhythmias or coronary artery disease, 11), sepsis (6), malignancy (2), anorexia nervosa (1). Age of normal controls and patients varied between 18 and 85 years. Sera were also obtained from cord bloods of 18 newborns, who had low $T_3$ syndrome. The criteria for diagnosis included clinical features, elevated free $T_3$ and/or free $T_4$ levels and suppressed serum TSH for hyperthyroidism; clinical features and low free $T_4$ concentration for hypothyroidism; low total serum total $T_3$ and high serum reverse $T_3$ (M) in nonthyroid illness (NTI) patients and newborns with the low $T_3$ syndrome. Serum TSH was clearly elevated (77±23 µU/ml, normal 0.3–4.7) in 12 patients with primary hypothyroidism. It was in the normal range or low in 13 other clinically hypothyroid patients with low serum free $T_4$ concentration. These patients either had a pituitary tumor, or they were recently hyperthyroid and had received treatment with antithyroid drugs or they were taking $T_4$ and were taken off $T_4$ in previous 2–3 weeks. The data in the latter group of patients have been analyzed both together with and separate from those in hypothyroid patients with elevated serum TSH. Serum TSH varied widely, between 0.05–10.9 μU/ml in patients with nonthyroidal illnesses (NTI). It was clearly normal in 18 of 25 patients. It was low (0.05–0.20) in 5 patients and elevated (7.9 and 10.9) in the remaining two patients with NTI. Serum free $T_4$ and free $T_3$ levels were in the normal range in 5 of 7 NTI patients with abnormal TSH. Serum free $T_4$ concentration was subnormal in the remaining two NTI patients who had low serum TSH. Seven of twenty-five NTI patients were considered to be seriously ill; six of them died in the hospitalization of study and the seventh one had low total $T_4$ as is frequently the case in moribund NTI patients. I. J. Chopra, "Euthyroid Sick Syndrome: Is it a misnomer", J Clin Endocrinol Metab. 1997;82:329–334. Eighteen of twenty-five NTI patients were considered to be moderately severely ill. They all had low serum total $T_3$, high reverse $T_3$, and they were discharged alive from the hospital; serum total $T_4$ was normal in all 15 patients with moderate NTI so studied. One NTI patient had recently received heparin when the blood was drawn, and two were taking arniodarone (200 mg/day). Two patients were receiving furosemide (10–20 mg/day) but their serum creatinine was 3 mg/dl or lower.

Two patients were receiving 25% dextrose as parenteral nutrition. NTI patients were not taking other drugs known to displace $T_4$ from TBG.

Example 3

Clinical Analyses Using Methods for the Determination of $T_3$ and $T_4$ by Equilibrium Dialysis and Radioimmunoassay Comparison of free $T_3$ and free $T_4$ concentrations measured separately and simultaneously.

Figure 3:
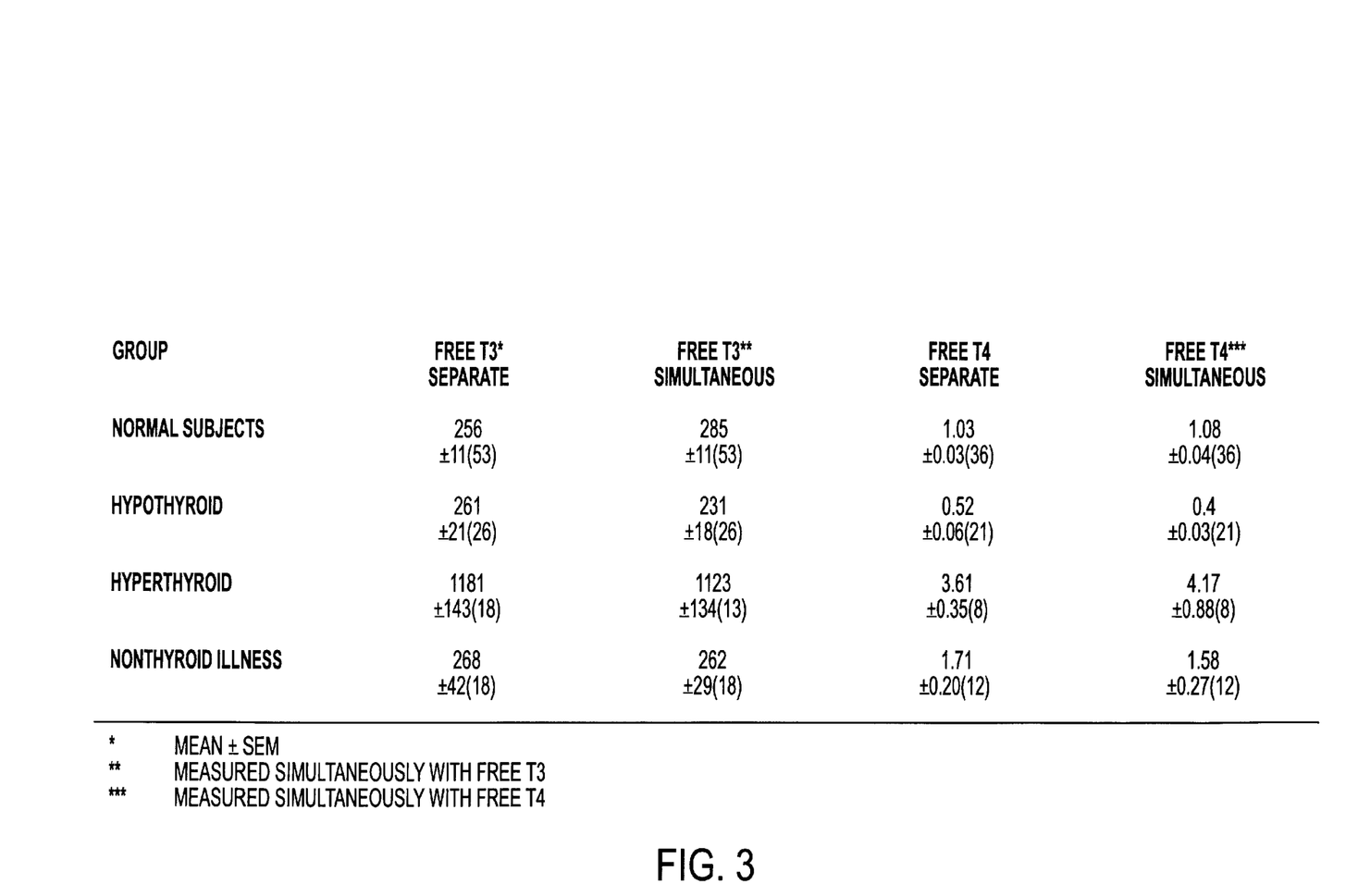
FIG. 3 is a Table which provides a comparison of free $T_3$ and free $T_4$ concentrations measured separately and simultaneously.

FIG. 3 compares free $T_3$ and free $T_4$ levels when measured, separately, or simultaneously. There was no appreciable, significant, or consistent difference in the values when measured simultaneously or separately.

Effect of $T_3$-spiking on free $T_3$ concentration in sera of NTI patients:

In order to examine the effect of adding exogenous unlabeled $T_3$ (200 ng/dl) on free $T_3$ concentration measured by our assay in sera of NTI patients, we studied free $T_3$ concentration in six NTI sera with and without spiking with exogenous unlabeled $T_3$ (200 ng/dl). The mean (±SEM) free $T_3$ concentration (138±26 pg/dl) with $T_3$-spiking, did not differ appreciably from the corresponding value (169±23 pg/dl) without $T_3$-spiking. We also examined, in four separate assays, free $T_3$ concentration in a pooled serum of hospitalized patients with and without spiking with $T_3$ (200 ng/dl). Free $T_3$ concentration in this pooled serum was (mean ±SEM, pg/dl) 309±25 without spiking and 370±56 after spiking with exogenous unlabeled $T_3$ (N.S.); serum concentration of total $T_3$ and total $T_4$ in this pooled serum were 70 ng/dl (normal 84–160) and 5.9 μg/dl (normal 5–13), respectively. In another study, we examined the effect of higher doses of added unlabeled $T_3$ on the dialyzable fraction of a pooled serum of hospitalized patients. We observed that the dialyzable fraction of $T_3$ was essentially unchanged with addition of up to 3 μg/dl $T_3$ to the serum. We also addressed a question asking whether a reduction in serum TBG concentration will lead to circumstances, whereby addition of exogenous unlabeled $T_3$ will cause an artefactual increase in serum free $T_3$ concentration. For this purpose, we measured in triplicate, percent free $T_3$ with and without adding 200 ng/dl of unlabeled $T_3$ to aliquots of ⅓ diluted pooled serum of hospitalized patients, The mean percent free $T_3$ after adding exogenous unlabeled $T_3$ did not differ significantly from that in diluted pooled serum without added $T_3$.

Reproducibility

The coefficient of variation (CV) for measurement of free $T_3$ in three serum pools tested seven times in an assay averaged 16.3%. The between assay CV measured in three serum pools tested 4–7 times over a six month period averaged 19.7%.

The coefficient of variation (CV) for measurement of free $T_4$ in three serum pools tested seven times in an assay averaged 15%. The between assay CV measured in three serum pools 4–7 times over a six month period averaged 17%.

Serum $T_4$ and $T_3$ Concentrations

Serum total $T_4$ was measured in 30 normal subjects and 20 patients with NTL. The mean (±SEM, μg/dl) serum $T_4$ value of 8.3±0.54 in NTI sera did not differ significantly from the corresponding value (8.1±0.47) in normal sera. However, the mean serum total $T_4$ (3.5±0.49) in 5 patients with severe NTI was significantly (P<0.001) lower than the corresponding value in normal sera. The mean serum total $T_4$ in 15 patients with moderately severe NTI was 9.9±0.6 (cf. normal P<0.05).

Serum total $T_3$ concentrations were measured in all patients studied (FIG. 4). The mean (±SEM, ng/dl) serum total $T_3$ was 113±2.7 in normal subjects. The mean serum $T_3$ was significantly decreased in hypothyroidism (90±8.3, P<0.005), NTI (46±5.0, P<0.001) and the newborn cord blood serum (50±3.31, P<0.001). It is notable that serum total $T_3$ was subnormal in all NTI patients and all newborn cord blood sera studied.

Serum Concentration of Free $T_3$ and Free $T_4$ in Health and Disease

Figure 1:
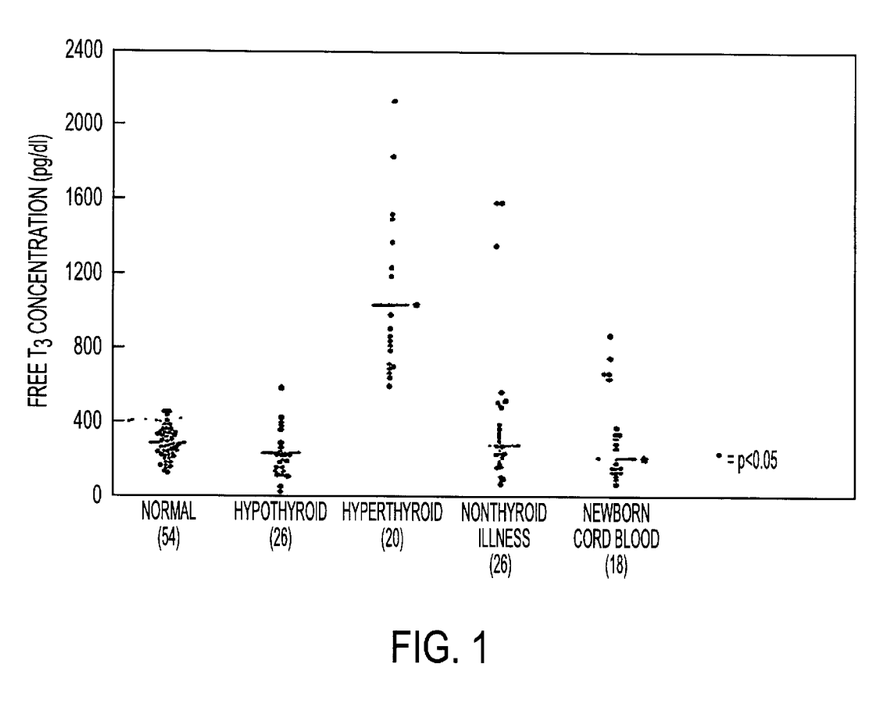
FIG. 1 illustrates serum free $T_3$ concentration in health and disease as measured by simultaneous assay for free $T_3$ and $T_4$ by equilibrium dialysis/RIA.
Figure 2:
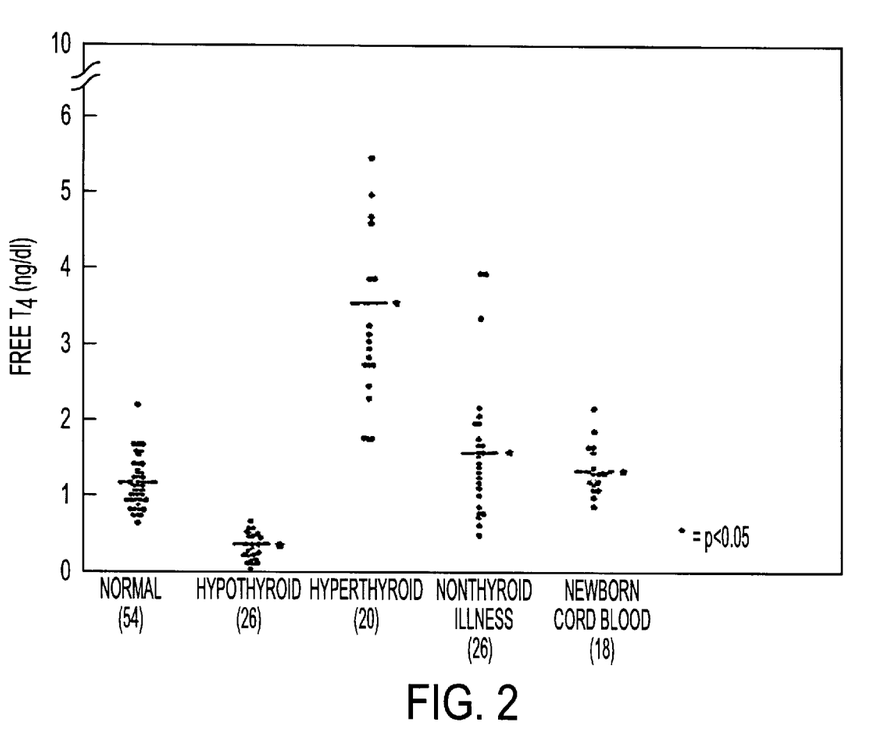
FIG. 2 illustrates serum free $T_4$ concentration in health and disease as measured by simultaneous assay for free $T_3$ and $T_4$ by equilibrium dialysis/RIA.

FIG. 4 describes the mean [±SEM, range] values for serum concentration of free $T_4$ free $T_3$, % free $T_4$, % free $T_3$, TSH, and reverse $T_3$ ($rT_3$) in various groups of patients studied; individual values of free $T_4$ and free $T_3$ concentrations in various groups of patients are shown in FIG. 1 and FIG. 2, respectively. The mean [±SE] free $T_4$ concentration (ng/dl) was 1.2±0.04 in sera of 54 normal subjects. It was significantly increased [3.6±0.4] in hyperthyroidism. Serum free $T_4$ concentration was clearly supranormal in 17 of 20 hyperthyroid patients studied; it was in the normal range in the remaining three hyperthyroid patients. Serum TSH was subnormal and free $T_3$ concentration was supranormal, in all 20 hyperthyroid patients studied. The mean serum free $T_4$ concentration (0.4±0.04) was clearly subnormal (P<0.001) in hypothyroid patients. Serum TSH was clearly supranormal (>10 μU/ml, normal 0.3–5.0) in 12 patients with primary hypothyroidism, whereas it was normal or low in remaining 14 hypothyroid patients who had pituitary and/or hypothalamic disease, had recently been withdrawn from thyroid hormone replacement or were previously hyperthyroid but had been overtreated with antithyroid drugs. The mean serum free $T_4$ concentration was mildly elevated [1.6±0.19, cf. normal P<0.05] in clinically euthyroid patients with systemic nonthyroid illnesses (NTIs) and in newborn cord blood sera [1.4±0.08, cf. normal P<0.05]. Serum free $T_4$ concentration was in the normal range in 22 out of 25 patients in patients with NTIs. It was elevated in the remaining three patients (FIG. 1); two of these 3 patients were receiving amiodarone and one patient had recently received treatment with heparin.

The mean [±SE] free $T_3$ concentration (pg/dl) was 285±10 in normal sera (FIG. 4, FIG. 2). It was clearly increased

[1033±98] in hyperthyroidism (P<0.001) and significantly decreased in hypothyroid patients with high TSH [175±23, P<0.001] and in newborn cord blood sera [204±22, P<0.005]. The mean serum free $T_3$ concentration in hypothyrold patients with low or normal TSH and in patients with systemic nonthyroid illnesses (NTIs) did not differ appreciably from the corresponding value in normal subjects (FIG. 2, FIG. 4). Even though serum total $T_3$ was clearly subnormal in all 25 patients with NTIs, the free $T_3$ concentration was clearly normal in most (21/25) patients; it was subnormal in remaining (4/25) patients. Three of the four patients with low serum free $T_3$ belonged to the group with severe 1M. However, the remaining four patients in this group with severe NTI had free $T_3$ levels in the normal range. Among 18 patients with moderately severe NTI, serum free $T_3$ concentration was clearly normal in 17 and low in one patient (FIG. 4). Similarly, free $T_3$ concentration was normal in 15 of 18 newborn cord blood sera while total serum $T_3$ was subnormal in all of them.

The discrepancy between free and total $T_3$ concentration in patients with NTIs and in newborn cord blood sera could be explained, in part at least, on the basis of elevated % free $T_3$. The mean % free $T_3$ was 0.30±0.1% in normal subjects. It was clearly elevated in patients with NTIs [0.70±0.6%, P<0.001] and in newborn cord blood sera [0.40±0.05, P<0.05]. The mean % free $T_3$ was also elevated in hyperthyroidism [0.5±0.04, P<0.001]. It was normal in hypothyroidism, however (FIG. 4). The data on % free $T_4$ values in NTI patients are also shown in FIG. 4. The changes in NTI patients were similar to those seen in % free $T_3$.

Many modifications and variations of the invention as hereinbefore set forth can be made without departing from the spirit and scope thereof and therefore only such limitations should be imposed as are indicated in the appended claims.

What is claimed is:

1. An immunoassay method for the simultaneous measurement of free thyroxine ($T_4$) and free triiodo-L-thyronine ($T_3$) thyroid hormone concentrations in a serum sample comprising the steps of:
    (a) dialyzing the serum sample to equilibrium in a physiological buffer system so that the free $T_3$ and the free $T_4$ are separated from $T_3$ and $T_4$ bound to serum proteins;
    (b) combining a measured quantity of the dialyzed serum sample having free $T_3$ and free $T_4$ with reagents comprising:
        (i) a measured quantity of $T_3$ labelled with a detectable marker and a measured quantity of $T_4$ labelled with a detectable marker;
        (ii) an anti-$T_3$ antibody of sufficient specificity and in sufficient quantity to bind a measurable quantity of the free $T_3$, and an anti-$T_4$ antibody of sufficient specificity and in sufficient quantity to bind a measurable quantity of the free $T_4$;
    (c) allowing reaction of the free $T_3$ and the free $T_4$ and the labelled $T_3$ and the labelled $T_4$, with the anti-$T_3$ antibody and the anti-$T_4$ antibody to proceed substantially to equilibrium to thereby produce antibody bound labelled $T_3$ and antibody bound labelled $T_4$;
    (d) separating the unbound labelled $T_3$ from the antibody bound labelled $T_3$ and the unbound labelled $T_4$ from the antibody bound labelled $T_4$; and
    (e) determining the concentrations of $T_3$ and $T_4$ in the sample by comparing relative amounts of antibody bound labelled $T_3$ and $T_4$ and unbound labelled $T_3$ and $T_4$.

2. An immunoassay method as set forth in claim 1 wherein a known quantity of exogenous unlabelled $T_3$ is added to the serum sample.

3. An immunoassay method as set forth in claim 1 wherein the anti-$T_3$ or anti-$T_4$ antibody is bound to a matrix comprising a portion of a container in which the immunoassay is performed.

4. An immunoassay method as set forth in claim 1 wherein the physiological buffer system comprises about 130 mmol of sodium, about 4.3 mmol of potassium, about 1.9 mmol of calcium, about 1.0 mmol of magnesium, about 98 mmol of chloride, about 1.3 mmol of phosphate, about 1.3 mmol of sulfate, about 5.4 mmol of lactate, about 3.3 mmol of glutamate, and about 8 mmol of urea.

5. An immunoassay as set forth in claim 4, wherein buffer system further comprises a preservative and gelatin.

6. An immunoassay method as set forth in claim 1 wherein the anti-$T_3$ and the anti-$T_4$ antibodies are polyclonal antibodies.

7. An immunoassay method as set forth in claim 1 wherein the incubation step is carried out at a temperature of about 4° C. for a period of about 20 hours.

8. An immunoassay method as set forth in claim 1 wherein the label is selected from the group consisting of iodine-125 and iodine-131.

9. The method of claim 1 wherein said antibody bound labelled thyroid hormone to be measured is separated from unbound labelled thyroid hormone by precipitation of the $T_3$ or the $T_4$ with an agent selected from the group consisting of: a second antibody, gamma globulin, a charcoal suspension and polyethylene glycol.

10. A radioimmunoassay method for the simultaneous measurement of free thyroxine ($T_4$) and free triiodo-L-thyronine ($T_3$) thyroid hormone concentrations in a serum sample comprising the steps of:
    (a) dialyzing the serum sample to equilibrium in a physiological buffer system so that the free $T_3$ and the free $T_4$ are separated from $T_3$ and $T_4$ bound to serum proteins;
    (b) combining a measured quantity of the dialyzed serum sample having free $T_3$ and free $T_4$ with reagents comprising:
        (i) a measured quantity of radiolabeled $T_3$ and a measured quantity of radiolabeled $T_4$;
        (ii) an anti-$T_3$ antibody of sufficient specificity and in sufficient quantity to bind a measurable quantity of the $T_3$, and an anti-$T_4$ antibody of sufficient specificity and in sufficient quantity to bind a measurable quantity of the $T_4$, wherein at least one antibody specific for $T_3$ or $T_4$ is bound to a matrix;
    (c) allowing reaction of the free $T_3$ and the free $T_4$ and the radioactive $T_3$ and the radioactive $T_4$, with the anti-$T_3$ antibody and the anti-$T_4$ antibody to proceed substantially to equilibrium to thereby produce antibody bound radioactive $T_3$ and antibody bound radioactive $T_4$;
    (d) separating the antibody bound radioactive $T_3$ from the antibody bound radioactive $T_4$,
    (e) separating the unbound radioactive $T_3$ from the antibody bound radioactive $T_3$ and the unbound radioactive $T_4$ from the antibody bound radioactive $T_4$;
    (f) measuring the quantity of antibody bound radioactive $T_3$ and $T_4$;
    (g) preparing a $T_3$ standard curve with known amounts of $T_3$ and preparing a $T_4$ standard curve with known amounts of $T_4$; and
    (h) comparing the quantity of radioactive $T_3$ measured with a known amount of $T_3$ read from the $T_3$ standard curve and correlating the quantity of radioactive $T_4$ measured with a known amount of $T_4$ read from the $T_4$ standard curve.

11. A radioimmunoassay method as set forth in claim 10 wherein a known quantity of exogenous unlabelled $T_3$ is added to the serum sample.

12. A radioimmunoassay method as set forth in claim 10 wherein the matrix to which the anti-$T_3$ or anti-$T_4$ antibody is bound comprises a portion of a container in which the radioimmunoassay is performed.

13. A radioimmunoassay method as set forth in claim 10 wherein the physiological buffer system comprises about 130 mmol of sodium, about 4.3 mmol of potassium, about 1.9 mmol of calcium, about 1.0 mmol of magnesium, about 98 mmol of chloride, about 1.3 mmol of phosphate, about 1.3 mmol of sulfate, about 5.4 mmol of lactate, about 3.3 mmol of glutamate, and about 8 mmol of urea.

14. An immunoassay as set forth in claim 13, wherein buffer system further comprises a preservative and gelatin.

15. A radioimmunoassay method as set forth in claim 10 wherein the anti-$T_3$ and the anti-$T_4$ antibodies are polyclonal antibodies.

16. A radioimmunoassay method as set forth in claim 10 wherein the incubation step is carried out at a temperature of about 4° C. for a period of about 20 hours.

17. A radioimmunoassay method as set forth in claim 10 wherein the radioactive label is iodine-125.

18. The method of claim 10 wherein said antibody bound radioactive thyroid hormone to be measured is separated from said free radioactive thyroid hormone by precipitation of the $T_3$ or the $T_4$ with an agent selected from the group consisting of: a second antibody, gamma globulin, a charcoal suspension and polyethylene glycol.

\* \* \* \* \*